United States Patent [19]
Leboulluec et al.

[11] Patent Number: 6,028,112
[45] Date of Patent: Feb. 22, 2000

[54] SPIROCYCLOPROPYL FLUORENES AS MELATONERGIC AGENTS

[75] Inventors: Karen L. Leboulluec, Durham; Katherine S. Takaki, Middletown, both of Conn.

[73] Assignee: Bristol-Myers Squibb Company, Princeton, N.J.

[21] Appl. No.: 09/126,976

[22] Filed: Jul. 31, 1998

Related U.S. Application Data

[63] Continuation-in-part of application No. 09/075,654, May 11, 1998, abandoned
[60] Provisional application No. 60/047,485, May 23, 1997.
[51] Int. Cl.$^7$ .......................... A61K 31/16; C07C 233/05
[52] U.S. Cl. .......................... 514/630; 514/530; 514/534; 514/538; 514/595; 514/624; 514/625; 514/627; 514/629; 560/27; 560/28; 564/57; 564/60; 564/189; 564/190; 564/204; 564/219; 564/220; 564/222
[58] Field of Search .............................. 564/57, 60, 189, 564/190, 204, 219, 220, 222; 514/624, 625, 627, 595, 530, 534, 538, 629, 630; 560/27, 28

[56] References Cited

U.S. PATENT DOCUMENTS

| | | |
|---|---|---|
| 3,419,604 | 12/1968 | Kaiser et al. . |
| 5,596,019 | 2/1997 | Mattson et al. . |

FOREIGN PATENT DOCUMENTS

| | | |
|---|---|---|
| 48729/93 | 10/1993 | Australia . |
| 420 064 | 4/1991 | European Pat. Off. . |
| 447 285 | 9/1991 | European Pat. Off. . |
| 506 539 | 9/1992 | European Pat. Off. . |
| 527 687 | 2/1993 | European Pat. Off. . |
| 530 087 | 3/1993 | European Pat. Off. . |
| 562 956 | 9/1993 | European Pat. Off. . |
| 747 346 | 12/1996 | European Pat. Off. . |
| WO 94/07487 | 4/1994 | WIPO . |

OTHER PUBLICATIONS

Arendt, J., et al., "Alleviation of Jet Lag by Melatonin: Preliminary Results of Controlled Double Blind Trial", Br. Med. J., 292, p. 1170 (May 1986).

Cassone, V. M., et al., "Dose–Dependent Entrainment of Rat Circadian Rhythms by Daily Injection of Melatonin", J. Biol. Rhythms, 1, (3), pp. 219–229 (1986).

Copinga, S., et al., "2–Amino–8–methoxytetralins: A Series of Nonindolic Melatonin–like–Agents", J. Med. Chem., 36, pp. 2891–2898 (1993).

Reppert, S. M., et al., "Cloning and Characterization of a Mammalian Melatonin Receptor That Mediates Reproductive and Circadian Responses", Neuron, 13, pp. 1177–1185(Nov., 1994).

Reppert, S. M., et al., "Molecular Characterization of a Second Melatonin Receptor Expressed in Human Retina and Brain: The Mel$_{1b}$ Melatonin Receptor ", Proc. Natl. Acad. Sci. USA, 92, pp. 8734–8738 (Sep. 1995).

Primary Examiner—Shailendra Kumar
Attorney, Agent, or Firm—Aldo A. Algieri

[57] ABSTRACT

There is provided novel spirocyclopropyl fluorene derivatives having the general Formula I

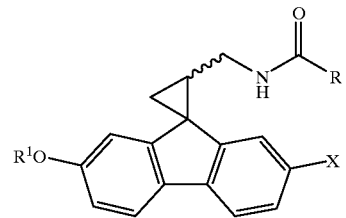

(I)

wherein R, $R^1$ and X are as defined herein which are useful as melatonergic agents.

9 Claims, No Drawings

SPIROCYCLOPROPYL FLUORENES AS MELATONERGIC AGENTS

CROSS-REFERENCE TO RELATED APPLICATION

This is a continuation-in-part application of application U.S. Ser. No. 09/075,654 filed May 11, 1998, now abandoned which claims the benefit of provisional application, U.S. Ser. No. 60/047,485 filed May 23, 1997.

BACKGROUND OF THE INVENTION

The invention pertains to novel substituted spirocyclopropyl fluorenes having drug and bio-affecting properties and to their preparation, pharmaceutical formulations and use. In particular, the invention concerns spirocyclopropylfluorenes having aminomethyl, methoxy and other substituents. These compounds possess melatonergic properties that should make them useful in treating certain medical disorders.

Melatonin (N-acetyl-5-methoxytryptamine) is a hormone which is synthesized and secreted primarily by the pineal gland. Melatonin levels show a cyclical, circadian pattern with highest levels occurring during the dark period of a circadian light-dark cycle. Melatonin is involved in the transduction of photoperiodic information and appears to modulate a variety of neural and endocrine functions in vertebrates, including the regulation of reproduction, body weight and metabolism in photoperiodic mammals, the control of circadian rhythms and the modulation of retinal physiology.

Recent evidence demonstrates that melatonin exerts its biological effects through specific receptors. Use of the biologically active, radiolabelled agonist $[^{125}I]$-2-iodomelatonin has led to the identification of high affinity melatonin receptors in the CNS of a variety of species. The sequences of two cloned human melatonin receptors have been reported [Reppert, et al., *Proc. Nat. Acad. Sci.* 92: 8734–8738 (1995) and Reppert, et al., *Neuron* 13: 1177–1185 (1994)]. In mammalian brain, autoradiographic studies have localized the distribution of melatonin receptors to a few specific structures. Although there are significant differences in melatonin receptor distribution even between closely related species, in general the highest binding site density occurs in discreet nuclei of the hypothalamus. In humans, specific $[^{125}I]$-2-iodomelatonin binding within the hypothalamus is completely localized to the suprachiasmatic nucleus, strongly suggesting the melatonin receptors are located within the human biological clock.

Exogenous melatonin administration has been found to synchronize circadian rhythms in rats (Cassone, et al., *J. Biol. Rhythms*, 1:219–229, 1986). In humans, administration of melatonin has been used to treat jet-lag related sleep disturbances, considered to be caused by desynchronization of circadian rhythms (Arendt, et al., *Br. Med. J.* 292:1170, 1986). Further, the use of a single dose of melatonin to induce sleep in humans has been claimed by Wurtman in International Patent Application WO 94/07487. Thus, melatonin agonists should be particularly useful for the treatment of sleep disorders and other chronobiological disorders. Melatonin agonists would also be useful for the further study of melatonin receptor interactions as well as in the treatment of conditions affected by melatonin activity, such as depression, jet-lag, work-shift syndrome, sleep disorders, glaucoma, reproduction, cancer, benign prostatic hyperplasia, premenstrual syndrome, inflammatory articular diseases, immune disorders, and neuroendorine disorders.

Aside from simple indole derivatives of melatonin itself, various bicyclic structures have been prepared and their use as melatonin ligands disclosed. In general these bicyclic amide structures can be represented as:

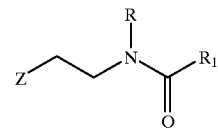

wherein Z is an aryl or heteroaryl system attached by a two carbon bridge to the amide group. Some specific examples follow.

Yous, et al. in European Patent Application EP-527,687A disclose as melatonin ligands arylethylamines i,

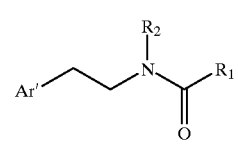

wherein Ar' is, inter alia, a substituted or unsubstituted benzo[b]thiophen-3-yl, benzimidazol-1-yl, benzo[b]furan-3-yl, 1,2-benzisoxazol-3-yl, 1,2-benzisothiazol-3-yl, or indazol-3-yl radical; $R_1$ is, inter alia, an alkyl or cycloalkyl group; and $R_2$ is hydrogen or lower alkyl.

Yous, et al. in European Patent Application EP-506,539A claim melatonin ligands ii,

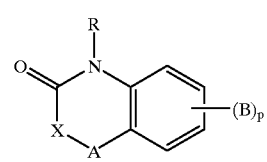

wherein A is oxygen or sulfur; X is a methylene group or a bond; and R is H or lower alkyl when p is 1 and B is defined by the radical iii,

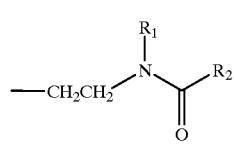

wherein $R_1$ is hydrogen or lower alkyl and $R_2$ is, inter alia, hydrogen, lower alkyl or cycloalkyl. Alternatively, R is defined by the radical iii when p is 0 or 1 and B is lower alkoxy.

Several naphthalene derivatives have also been disclosed as melatonin ligands.

Andrieux, et al. in European Patent Application EP-447,285A claim amidoalkylnaphthalenes iv,

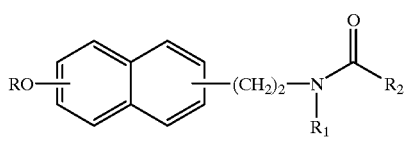

wherein R is lower alkyl; $R_1$ is hydrogen or lower alkyl; and $R_2$ is, inter alia, hydrogen, lower alkyl, or cycloalkyl.

Yous, et al. in European Patent Application EP-562,956A disclose amide and urea naphthalene derivatives v,

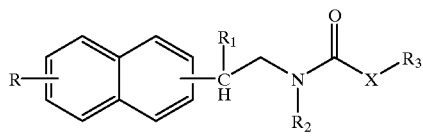

in which R is hydrogen or $OR_4$ wherein $R_4$ is, inter alia, hydrogen, alkyl, cycloalkyl, or cycloalkylalkyl; $R_1$ is hydrogen or $COOR_5$ wherein $R_5$ is hydrogen or alkyl; $R_2$ is hydrogen or alkyl; X is NH or a bond; and $R_3$ is, inter alia, alkyl, alkenyl, or cycloalkyl.

Lesieur, et al. in European Patent Application EP-530,087A disclose naphthylethylureas and naphthylethylthioureas vi,

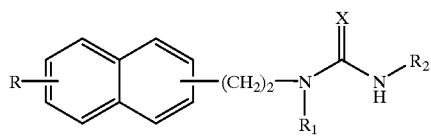

in which R is hydrogen or $OR_3$ wherein $R_3$ is, inter alia, hydrogen, lower alkyl, or cycloalkyl; $R_1$ is hydrogen or lower alkyl; X is oxygen or sulfur; and $R_2$ is, inter alia, lower alkyl or cycloalkyl.

Langlois, et al., in Australian Patent Application AU-A-48729/93 disclose arylalkyl(thio)amides vii as melatonergic ligands,

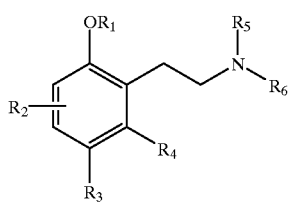

wherein $R_1$ is hydrogen or lower alkyl; $R_2$ is hydrogen, halogen, or lower alkyl; $R_3$ and $R_4$ are identical or different groups including, inter alia, hydrogen, halogen, or lower alkyl or $R_3$ and $R_4$, together with the benzene ring which carries them, form a ring-system $E_3$ chosen from, inter alia, naphthalene, on the understanding that the portion of the ring-system $E_3$ formed by $R_3$ and $R_4$ and the two carbon atoms of the benzene ring which carry them is unhydrogenated or partially hydrogenated; $R_5$ is hydrogen or lower alkyl; and $R_6$ is,

wherein X is sulfur or oxygen and $R_7$ is, inter alia, lower alkyl or alkenyl.

Horn and Dubocovich in European Patent Application EP-420,064A disclose 2-amidotetralins viii as melatonin ligands,

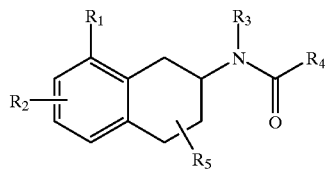

wherein $R_1$ is, inter alia, hydrogen, lower alkyl, or lower alkoxyl; $R_2$ is, inter alia, hydrogen, halogen, or lower alkoxyl; $R_3$ is, inter alia, hydrogen, or lower alkyl; $R_4$ is, inter alia, lower alkyl, haloalkyl or cycloalkyl; and $R_5$ is hydrogen, hydroxyl, halogen, oxo, aryl, lower alkyl or alkylaryl.

Copinga et al, in *J. Med. Chem.*, 1993, 36, p. 2891, discusses amidomethoxytetralins of structure ix and their melatonergic properties.

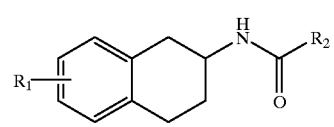

In structure ix, $R_1$ is H or $OCH_3$ and $R_2$ is alkyl, haloalkyl, phenylalkyl or phenyl.

U.S. Pat. No. 3,419,604 discloses antidepressant compounds of structure x:

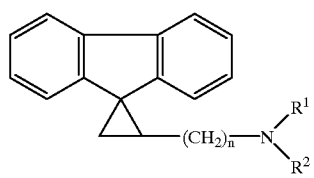

wherein n=0–2, and $R^1$ and $R^2$ are hydrogen, lower alkyl or are taken together in a cyclic amino group.

U.S. Pat. No. 5,596,019 and European Patent EP-747,346 A2 disclose, respectively, N-acyl-cycloalkylamine derivatives and N-acyl-2-aryl cyclopropylmethylamine derivatives which are useful as melatonergic agents.

The foregoing disclosures do not teach or suggest the novel melatonergic spirocyclopropylfluorenes of the present invention. The novel compounds of the present invention are melatonergic agonists with good affinity for human melatonin receptors which should make them useful for treating disorders associated with the melatonergic system.

SUMMARY OF THE INVENTION

The present invention provides novel spirocyclopropylfluorene derivatives having the general Formula I

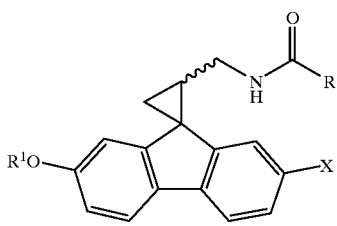

wherein R, $R^1$ and X are as defined below, including hydrates and solvates thereof which bind to the human melatonergic receptor and therefore are useful as melatonergic agents in the treatment of sleep disorders, seasonal depression, shifts in circadian cycles, melancholia, stress, appetite regulation and related conditions.

DETAILED DESCRIPTION OF THE INVENTION

The present invention provides a novel series of melatonergic compounds including hydrates and solvates thereof having the Formula I:

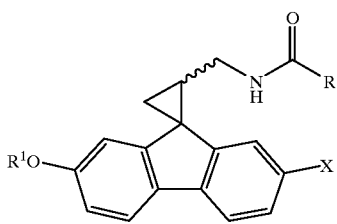

wherein:

R is $C_{1-4}$ alkyl, $C_{3-6}$ cycloalkyl, $C_{1-3}$ haloalkyl, $C_{1-6}$ alkylamino, di($C_{1-6}$) alkylamino, $C_{3-6}$ cycloalkylamino, $C_{2-6}$ alkenyl, $C_{2-4}$ alkoxyalkyl, $C_{1-4}$ trihalomethylalkyl, or $C_{2-8}$ alkylthioalkyl;

X is $C_{1-4}$ alkoxy, hydrogen or halogen; and $R^1$ is $C_{1-6}$ alkyl.

The present invention also provides a method for the treatment of sleep disorders and related conditions, which comprises administering a therapeutically effective amount of a compound of Formula I or a solvate or hydrate thereof.

R is $C_{1-4}$ alkyl, $C_{3-6}$ cycloalkyl, $C_{1-3}$ haloalkyl, $C_{1-6}$ alkylamino, di($C_{1-6}$) alkylamino, $C_{3-6}$ cycloalkylamino, $C_{2-6}$ alkenyl, $C_{2-4}$ alkoxyalkyl, $C_{1-4}$ trihalomethylalkyl, or $C_{2-8}$ alkylthioalkyl. Methyl, ethyl, n-propyl and cyclopropyl are preferred R groups.

X is $C_{1-4}$ alkoxy, hydrogen or halogen. It is preferred that X be $OCH_3$ or F, with $OCH_3$ most preferred.

"Alkyl" means a monovalent straight or branched chain group of the formula $C_mH_{2m+1}$, with m being the number of carbon atoms.

"Cycloalkyl" groups are monovalent cyclic moieties containing at least 3 carbon atoms and conforming to the formula $C_mH_{(2m-1)}$, with m being the number of carbon atoms present.

"Alkoxy" refers to monovalent substituents of the structure: —O-alkyl.

By "haloalkyl" is meant alkyl groups having from 1 to 3, Br, Cl, F or I halogen atoms.

The term "alkenyl" refers to ethylenically unsaturated groups containing one site of unsaturation and having from 2 to 6 carbon atoms.

By "alkoxyalkyl" is meant moieties of the formula -alkyl-O-alkyl having the indicated total number of carbon atoms.

"Trihalomethylalkyl" groups are groups having the formula -alkyl-C(Hal)$_3$, in which "Hal" designates a halogen atom. Trifluoromethylalkyl groups are preferred.

Useful "alkylthioalkyl" groups have the structure -alkyl-S-alkyl and contain the indicated total number of carbon atoms.

Preferred compounds have $IC_{50}$ values of 250 nM or less in melatonergic binding tests described herein.

One group of preferred compounds include those of Formula I in which X is methoxy or fluorine; and R is $C_{1-6}$ alkyl.

Preferred compounds include:

N-[(2',7'-dimethoxyspiro[cyclopropane-1,9'-[9H]fluoren]-2-yl)methyl]acetamide;

N-[(2',7'-dimethoxyspiro[cyclopropane-1,9'-[9H]fluoren]-2-yl)methyl]propanamide;

N-[(2',7'-dimethoxyspiro[cyclopropane-1,9'-[9H]fluoren]-2-yl)methyl]butanamide;

(+)-N-[(2',7'-dimethoxyspiro[cyclopropane-1,9'-[9H]fluoren]-2-yl)methyl]propanamide;

(−)-N-[(2',7'-dimethoxyspiro[cyclopropane-1,9'-[9H]fluoren]-2-yl)methyl]propanamide;

cis-N-[(2'-fluoro-7'-methoxy-spiro[cyclopropane-1,9'-[9H]fluoren]-2-yl)methyl]propanamide;

trans-N-[(2'-fluoro-7'-methoxy-spiro[cyclopropane-1,9'-[9H]fluoren]-2-yl)methyl]propanamide;

N-[(2',7'-dimethoxyspiro[cyclopropane-1,9'-[9H]fluoren]-2-yl)methyl]cyclopropane carboxamide; and N-[(2',7'-dimethoxyspiro[cyclopropane-1,9'-[9H]fluoren]-2-yl)methyl]cyclobutane carboxamide.

Additionally, compounds of Formula I encompass all pharmaceutically acceptable solvates, particularly hydrates, thereof. The present invention also encompasses stereoisomers as well as optical isomers, e.g. mixtures of enantiomers including racemic mixtures, as well as individual enantiomers and diastereomers, which arise as a consequence of structural asymmetry in certain compounds of Formula I. Separation of the individual isomers is accomplished by application of various methods which are well known to practitioners in the art.

Compounds of Formula I can be prepared using the overall process shown in the following scheme:

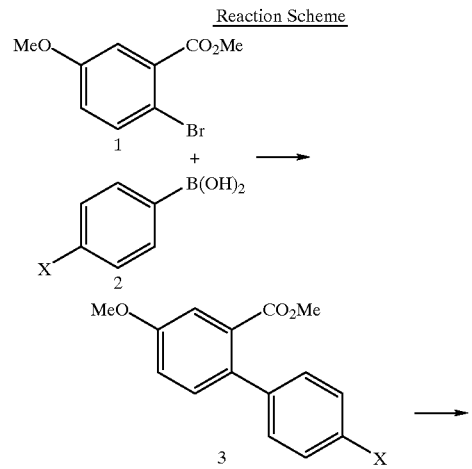

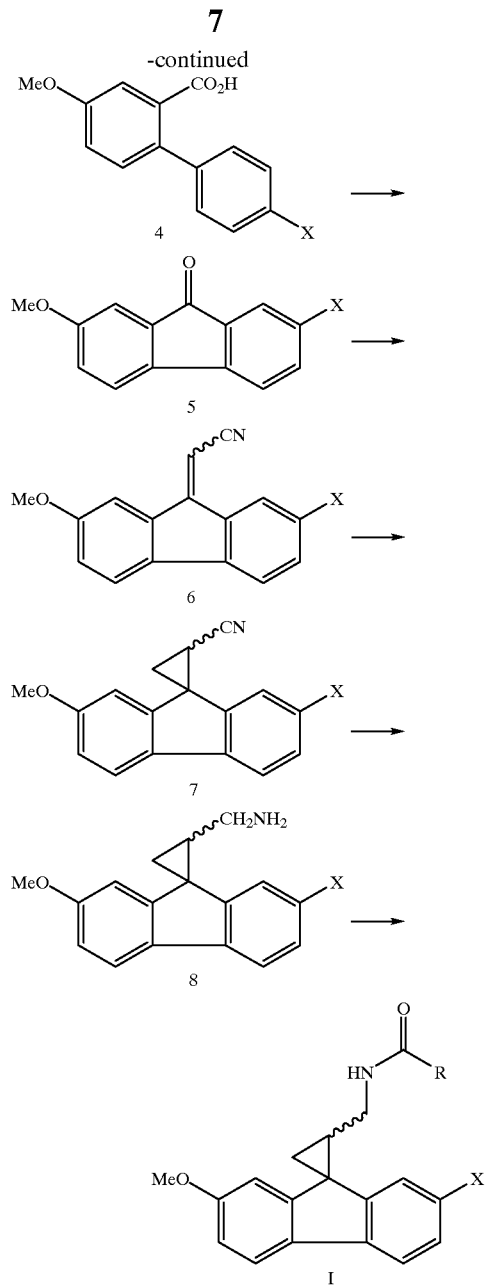

converted to the unsaturated nitrile derivative 6 by treatment with reagents such as diethyl cyanomethylphosphonate and a strong base such as sodium hydride or sodium ethoxide. Intermediate 6 can be cyclopropanated using reagents such as trimethylsulfoxonium iodide and sodium hydride in solvents such as DMF, THF, or the like. Subsequent reduction of the cyclopropane derivatives 7 using reagents such as borane-dimethyl sulfide complex in methylene chloride or LAH in THF or ether provides the amine intermediate 8. Further reaction of 8 with acylating reagents gives compounds of formula I. Suitable acylating agents include carboxylic acid halides, anhydrides, acyl imidazoles, alkyl isocyanates, and carboxylic acids in the presence of condensing agents such as carbonyl imidazole, carbodiimides, and the like.

The Biological Activity of the Compounds

The compounds of the invention are melatonergic agents. They have been found to bind human melatonergic receptors expressed in a stable cell line with good affinity. Further, the compounds are agonists as determined by their ability, like melatonin, to block the forskolin-stimulated accumulation of cAMP in certain cells. Due to these properties, the compounds and compositions of the invention should be useful as sedatives, chronobiotic agents, anxiolytics, antipsychotics, analgesics, and the like. Specifically, these agents should find use in the treatment of stress, sleep disorders, seasonal depression, appetite regulation, shifts in circadian cycles, melancholia and related conditions.

Melatonergic Receptor Binding Activity

1. Reagents:
   (a) TME=50 mM Tris buffer containing 12.5 mM $MgCl_2$, and 2 mM EDTA, pH 7.4 at 37° C. with concentrated HCl.
   (b) Wash buffer: 20 mM Tris base containing 2 mM $MgCl_2$. pH 7.4 at room temperature.
   (c) $10^{-4}$M melatonin ($10^{-5}$M final concentration).
   (d) 2-[$^{125}$I]-iodomelatonin, 0.1M final concentration 2. Membrane Homogenates. The melatonin $ML_{1A}$ receptor cDNA was subcloned into pcDNA3 and introduced into NIH-3T3 cells using Lipofectamine. Transformed NIH-3T3 cells resistant to geneticin (G-418) were isolated, and single colonies expressing high levels of 2[$^{125}$I]iodomelatonin binding were isolated. Cells are maintained in DMEM supplemented with 10% calf serum and G-418 (0.5 g/liter). Cells are grown to confluency in T-175 flasks, scraped using Hank's balanced salt solution, and frozen at −80° C. For preparing membrane homogenates, pellets are thawed on ice, and resuspended in TME buffer in the presence of 10 μg/ml aprotinin and leupeptin, and 100 μM phenylmethylsulfonylfluoride. The cells were then homogenized using a dounce homogenizer, and centrifuged. The resulting pellet was resuspended with dounce homogenizer in TME (supplemented with the above protease inhibitors) and frozen. On the day of assay, the small aliquot was thawed on ice and resuspended in ice cold TME (1:50–1:100 v/v) and held on ice until assayed.

3. Incubation: 37° C. for 1 hour. Reaction is terminated by filtration. Filters are washed 3 times.

4. References: Reppert, S. M., and Ebisawa, R. (1994). *Neuron*, 13, 1177–1185.

The intermediate biphenyl derivatives 3 can be prepared by the coupling of methyl 2-bromo-5-methoxy benzoate with an appropriately substituted phenyl boronic acid in the presence of a palladium catalyst such as tris(dibenzylideneacetone)dipalladium (0) or palladium (II) acetate and a base such as sodium carbonate, sodium hydroxide, potassium fluoride, or potassium phosphate in solvents such as DME, benzene, THF or acetone. The resulting biphenyl ester derivative 3 is hydrolyzed using standard conditions to provide the biphenyl carboxylic acid 4. Intramolecular cyclization to the fluorenone derivative 5 can be accomplished directly by heating 4 in PPA or refluxing thionyl chloride. Alternatively, 4 can be converted to the acid chloride using reagents such as thionyl chloride, phosphoryl chloride or the like and the acid chloride can be subsequently cyclized to 5 by treatment with a strong Lewis acid such as aluminum chloride. The fluorenone can be The binding data for some compounds of Formula I are shown in the table below.

TABLE

Melatonergic Binding Data for Some Formula I Compounds

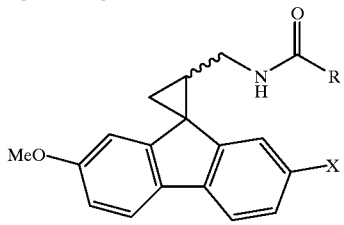

| Ex | Melatonin Binding Affinity (IC$_{50}$ Range) | Compound Name |
|---|---|---|
| 3 | *** | N-[(2',7'-dimethoxyspiro[cyclopropane-1,9'-[9H]fluoren]-2-yl)methyl]propanamide |
| 4 | *** | (−)-N-[(2',7'-dimethoxyspiro[cyclopropane-1,9'-[9H]fluoren]-2-yl)methyl]propanamide |
| 5 | *** | (+)-N-[(2',7'-dimethoxyspiro[cyclopropane-1,9'-[9H]fluoren]-2-yl)methyl]propanamide |
| 6 | *** | N-[(2',7'-dimethoxyspiro[cyclopropane-1,9'-[9H]fluorene]-2-yl)methyl]acetamide |
| 7 | *** | N-[(2',7'-dimethoxyspiro[cyclopropane-1,9'-[9H]fluorene]-2-yl)methyl]butanamide |
| 8 | *** | N-[(2',7'-dimethoxyspiro[cyclopropane-1,9'-[9H]fluoren]-2-yl)methyl]cyclopropane carboxamide |
| 9 | ** | N-[(2',7'-dimethoxyspiro[cyclopropane-1,9'-[9H]fluoren]-2-yl)methyl]cyclobutane carboxamide |
| 10 | * | N-[(2',7'-dimethoxyspiro[cyclopropane-1,9'-[9H]fluoren]-2-yl)methyl]-2,2-dimethylpropanamide |
| 12 | *** | cis-N-[(2'-fluoro-7'-methoxy-spiro[cyclopropane-1,9'-[9H]fluoren]-2-yl)methyl]propanamide |
| 13 | *** | trans-N-[(2'-fluoro-7'-methoxy-spiro[cyclopropane-1,9'-[9H]fluoren]-2-yl)methyl]propanamide |

*: 250 nM > IC$_{50}$ > 100 nM
**: 100 nM > IC$_{50}$ > 10 nM
***: 10 nM > IC$_{50}$

In making pharmaceutical compositions containing compounds of the present invention, the active ingredient(s) will usually be mixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. Thus, the composition can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelatin capsules, suppositories, sterile injectable solutions and sterile packaged powders.

Some examples of suitable carriers and diluents include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, methyl cellulose, methyl- and propylhydroxybenzoates, talc, magnesium stearate and mineral oil. The formulations can additionally include lubricating agents, wetting agents, emulsifying and suspending agents, preserving agents, sweetening agents or flavoring agents. The compositions of the invention may be formulated so as to provide quick, sustained or delayed release of the active ingredient after administration to the patient.

The compositions are preferably formulated in a unit dosage form, each dosage containing from about 0.1 to 500 mg, more usually 1 to 100 mg, of the active ingredient. The term "unit dosage form" refers to physically discrete units suitable as unitary dosages for human subjects and other mammals, each unit containing a predetermined quantity of active material calculated to produce the desired therapeutic effect, in association with the required pharmaceutical carrier.

These active compounds are effective over a wide dosage range. For example, dosages per day will normally fall within the range of about 0.1 to 500 mg. In the treatment of adult humans, the range of about 0.1 to 100 mg/day, in single or divided doses, is preferred. Generally, the compounds of the invention may be used in treating sleep and related disorders in a manner similar to that used for melatonin.

However, it will be understood that the amount of the compound actually administered will be determined by a physician, in the light of the relevant circumstances including the condition to be treated, the choice of compound to be administered, the chosen route of administration, the age, weight, and response of the individual patient, and the severity of the patient's symptoms.

The compounds which constitute this invention, their methods of preparation and their biologic actions will appear more fully from consideration of the following examples, which are given for the purpose of illustration only and are not to be construed as limiting the invention in sphere or scope.

DESCRIPTION OF SPECIFIC EMBODIMENTS

In the following examples, used to illustrate the foregoing synthetic processes, all temperatures are expressed in degrees Celsius and melting points are uncorrected. Proton magnetic resonance ($^1$H NMR) and carbon magnetic resonance ($^{13}$C NMR) spectra were determined in the solvents indicated and chemical shifts are reported in δ units downfield from the internal standard tetramethylsilane (TMS) and interproton coupling constants are reported in Hertz (Hz). Splitting patterns are designated as follows: s, singlet; d, doublet; t, triplet; q, quartet; m, multiplet; br, broad peak; dd, doublet of doublet; bd, broad doublet; dt, doublet of triplet; bs, broad singlet; dq, doublet of quartet. The infrared (IR) spectral descriptions include only absorption wave numbers (cm$^{-1}$) having functional group identification value. The IR determinations were employed using the compound neat as a film or by employing potassium bromide (KBr) as diluent. Optical rotations $[\alpha]_D^{25}$ were determined on a Perkin-Elmer 41 polarimeter in the solvents and concentration indicated. The elemental analyses are reported as percent by weight.

General Procedure for Preparing the Intermediate Fluorenones (5)

The intermediate fluorenones (5) necessary for the preparation of the compounds of the invention were obtained commercially or prepared analogously to the following procedure illustrated below:

2-Fluoro-7-methoxyfluorenone

Methyl-2-bromo-5-methoxybenzoate (15.1 g; 0.062 mol), 4-fluorobenzene boronic acid (9.98 g; 0.0713 mol), and tris(dibenzylideneacetone)dipalladium (0) (1.0 g) were dissolved in 100 mL dimethoxyethane (DME) and 100 mL 2N sodium carbonate and stirred at reflux overnight. The reaction mixture was cooled, the DME removed in vacuo, and the resulting oil partitioned between methylene chloride and water. The aqueous layer was extracted further with methylene chloride and the combined organic extracts dried over magnesium sulfate and concentrated in vacuo. Purification of the crude material by silica gel column chromatography (gradient elution with ethyl acetate/hexane) provided 5-methoxy-[2-(4-fluorophenyl)] benzoic acid methyl ester as a colorless oil (63%). The ester (8.6 g) was hydrolyzed in refluxing 1N sodium hydroxide (72 mL) and ethanol (250 mL). The reaction mixture was cooled and extracted with ethyl acetate. The aqueous layer was then acidified, extracted with EtOAc and the extracts concentrated to afford pure 5-methoxy-[2-(4-fluorophenyl)] benzoic acid in 86% yield. The acid (6.9 g; 0.03 mol) was dissolved in 50 mL thionyl chloride and refluxed overnight. The thionyl chloride was removed in vacuo to afford 2-fluoro-7-methoxy fluorenone quantitatively as an orange solid.

General Procedure for Preparing the Intermediate Amines (8)

The intermediate fluorenones (5) were converted to the intermediate amines (8) analogously to the following procedure:

[2'-Fluoro-7'-methoxy spiro(cyclopropane-1,9'-[9H] fluoren)-2-yl]methanamine

Step A. Sodium hydride (0.7 g of 60% dispersion in mineral oil, 17.5 mmol) was washed with hexane and suspended in 20 mL of anhydrous tetrahydrofuran (THF) under a nitrogen atmosphere. Diethylcyanomethylphosphonate (3.4 g, 19 mmol) was added slowly in portions over 15 min and the reaction mixture was stirred for 30 min at room temperature. 2-Fluoro-7-methoxy fluorenone (4.4 g, 19 mmol) dissolved in 30 mL THF was added in portions and the reaction was refluxed overnight. The crude reaction mixture was cooled to room temperature and then poured into 150 mL water and extracted with several portions of ethyl acetate. The combined organic layers were dried over magnesium sulfate and concentrated in vacuo to provide the unsaturated nitrile (5.6 g) as a red-orange solid which was used without further purification.

Step B. Sodium hydride (1.2 g of a 60% dispersion in mineral oil, 30 mmol) was washed with hexane and suspended in 100 mL anhydrous dimethyl sulfoxide (DMSO) under a nitrogen atmosphere. Trimethyl-sulfoxoniumiodide (11 g, 50 mmol) was added in portions to the heterogeneous reaction mixture which was stirred until the foaming subsided. The reaction was cooled to 0° C. and the α,β-unsaturated nitrile (4 g; 16 mmol) dissolved in 40 mL anhydrous DMSO was added in portions over 20 min. The reaction was allowed to warm to room temperature with stirring overnight during which time a black precipitate formed. The crude reaction mixture was slowly poured into saturated aqueous ammonium chloride solution and the resulting mixture was further diluted with ethyl acetate. The phases were separated and the aqueous layer was extracted several times with ethyl acetate. The combined organic fractions were dried over magnesium sulfate and concentrated in vacuo to a light brown oil (6.3 g). The diastereomeric mixture of spirocyclopropylnitriles was separated by silica gel column chromatography (gradient elution with ethyl acetate and hexanes) to provide the two diastereomers in a combined yield of 35% for the two steps, A and B.

Step C. Each diastereomer was converted separately to the amine. The spirocyclopropylnitrile (0.74 g) was stirred at reflux in 20 mL THF. Four equivalents of borane-dimethyl sulfide complex (1.0 M in methylene chloride) was added in several portions and the reaction mixture was refluxed for 30 minutes. The reaction was cooled, 6N hydrochloric acid (5 mL) was added dropwise, and the reaction mixture was refluxed for 30 min. The reaction mixture was brought to a basic pH and extracted several times with methylene chloride. The combined organic extracts were dried over magnesium sulfate and concentrated in vacuo to provide the crude amine which was purified by silica gel column chromatography (MeOH/EtOAc) then converted to the salt upon treatment with concentrated hydrochloric acid (0.38 g; yield 33%).

General Procedure for Preparation of Compounds of Formula (I)

The intermediate amines (8) were converted to the compounds of Formula (I) analogously to the following procedure:

The amine hydrochloride salt obtained via the above general procedure (250 mg; 0.8 mmol) was stirred in acetonitrile and triethylamine (0.25 mL; 1.8 mmol) for 15 min under a nitrogen atmosphere. The appropriate acid chloride (0.8 mmol) was added dropwise and the reaction stirred at room temperature for 30 min. The reaction mixture was diluted with ethyl acetate, washed with 1N hydrochloric acid and 1N sodium hydroxide solutions and then dried over magnesium sulfate and concentrated in vacuo. The crude products were crystallized from ethyl acetate or purified by silica gel column chromatography.

Compounds of Formula (I) were prepared as racemates and in some cases resolved by chiral HPLC separation using either an analytical Chiralcel-OD column or preparative Daicel column with an isocratic mobile phase of 10–15% isopropyl alcohol and hexane.

The following examples illustrate the preparation of the compounds of the invention by following the general procedures described above.

EXAMPLE 1

(2',7'-Dimethoxyspiro[cyclopropane-1,9'-[9H] fluoren]-2-yl)nitrile

The crude material, obtained as a light brown oil was purified by silica gel column chromatography using an ethyl acetate/hexanes gradient. The desired product was obtained in 43% from 2,7-dimethoxy fluorenone (mp=131–133° C.; light yellow solid): $^1$H-NMR (CDCl$_3$) δ 7.59 (d, J=8.4 Hz, 1H), 7.57 (d, J=8.3 Hz, 1H), 6.94 (dd, J=8.3, 2.3 Hz, 1H), 6.86–6.91 (m, 2H), 6.43 (d, J=2.3 Hz, 1H), 3.85 (s, 3H), 3.80 (s, 3H), 2.30–2.36 (m, 1H), 2.04–2.15 (m, 2H); $^{13}$C-NMR (CDCl$_3$) δ 158.8, 158.7, 144.9, 142.2, 133.4 (2), 120.2, 120.1, 117.7, 114.0, 112.9, 107.5, 106.7, 104.8, 55.5, 34.8, 21.7, 14.8; FTIR (KBr) 2237, 1623, 1582, 1470 cm$^{-1}$;

Anal. Calcd. for C$_{18}$H$_{15}$NO$_2$: C, 77.96; H, 5.45; N, 5.05. Found: C, 77.80; H, 5.49; N, 5.00.

EXAMPLE 2

[2',7'-Dimethoxyspiro(cyclopropane-1,9'[9H]fluoren)-2-yl]methanamine

The desired amine was isolated as the hydrochloride salt in 35% yield. (mp>250° C.): $^1$H-NMR (DMSO) δ 8.28 (br s, 2H), 7.73 (d, J=8.3 Hz, 1H), 7.68 (d, J=8.3 Hz, 1H), 7.03 (d, 1H, J=1.9 Hz), 6.87–6.94 (m, 2H), 6.67 (d, 1H, J=2.0 Hz), 3.81 (s, 3H), 3.78 (s, 3H), 3.08–3.27 (m, 2H), 2.00–2.17 (m, 3H); $^{13}$C-NMR (DMSO) δ 158.5, 157.9, 148.8, 144.7, 133.5, 131.8, 120.1, 119.8, 112.2, 112.1, 108.3, 104.8, 55.5, 55.3, 37.2, 34.0, 27.7, 21.1.

EXAMPLE 3

N-[(2',7'-Dimethoxyspiro[cyclopropane-1,9'-[9H]fluoren]-2-yl)methyl]propanamide A white solid was obtained in 72% after silica gel column chromatography; mp=145–147° C.: $^1$H-NMR (CDCl$_3$) δ 7.64 (d, J=8.3 Hz, 1H), 7.59 (d, J=8.3 Hz, 1H), 6.84–6.92 (m, 2H), 6.78 (d, 1H, J=2.3 Hz), 6.49 (d, 1H, J=2.3 Hz), 5.26 (br s, 1H), 4.15–4.25 (m, 1H), 3.84 (s, 3H), 3.82 (s, 3H), 3.20–3.29 (m, 1H), 1.87–2.12 (m, 4H), 1.66–1.70 (m, 1H), 0.96 (t, 3H, J=7.6 Hz); $^{13}$C-NMR (CDCl$_3$) δ 173.6, 158.9, 158.3, 149.6, 145.5, 134.0, 132.2, 120.1, 119.7, 112.0 (2), 107.6, 104.4, 55.6, 55.5, 38.6, 33.6, 31.4, 29.5, 22.8, 9.6; FTIR (KBr) 3311, 1638, 1469, 1212 cm$^{-1}$;

Anal. Calcd. for C$_{21}$H$_{23}$NO$_3$: C, 74.75; H, 6.87; N, 4.15. Found: C, 74.51; H, 6.83; N, 4.02.

EXAMPLE 4

(−)-N-[(2'7'-Dimethoxyspiro[cyclopropane-1,9'-[9H]fluoren]-2-yl)methyl]propanamide A white solid was obtained in 10% yield after chiral HPLC separation; optical rotation: −90.952 (1.052 mg/cc in methanol); mp=150–151° C.: $^1$H-NMR (CDCl$_3$) δ 7.64 (d, J=8.3 Hz, 1H), 7.59 (d, J=8.3 Hz, 1H), 6.85–6.92 (m, 2H), 6.77 (d, 1H, J=2.1 Hz), 6.49 (d, 1H, J=2.2 Hz), 5.25 (br s, 1H), 4.18–4.23 (m, 1H), 3.84 (s, 3H), 3.82 (s, 3H), 3.21–3.28 (m, 1H), 1.88–2.09 (m, 4H), 1.66–1.71 (m, 1H), 0.96 (t, 3H, J=7.3 Hz); $^{13}$C-NMR (CDCl$_3$) δ 159.0, 158.4, 149.6, 145.5, 134.1, 132.2, 120.1, 119.7, 112.1, 112.0, 107.6, 104.4, 55.7, 55.6, 38.7, 33.7, 31.4, 29.5, 22.8, 9.6; FTIR (KBr) 3303, 2944, 1636, 1554, 1470 cm$^{-1}$.

EXAMPLE 5

(+)-N-[(2',7'-Dimethoxyspiro[cyclopropane-1,9'-[9H]fluoren]-2-yl)methyl]propanamide A white solid was obtained after chiral HPLC separation and recrystallization; optical rotation: +79.589 (0.74 mg/cc in methanol); mp=138–141° C.: $^1$H-NMR (CDCl$_3$) δ 7.65 (d, J=8.3 Hz, 1H), 7.60 (d, J=8.3 Hz, 1H), 6.85–6.92 (m, 2H), 6.77 (d, 1H, J=2.3 Hz), 6.49 (d, 1H, J=2.3 Hz), 5.18 (br s, 1H), 4.18–4.27 (m, 1H), 3.84 (s, 3H), 3.82 (s, 3H), 3.20–3.29 (m, 1H) 1.89–2.13 (m, 4H), 1.67–1.71 (m, 1H), 0.96 (t, 3H, J=7.6 Hz); $^{13}$C-NMR (CDCl$_3$) δ 173.7, 159.0, 158.4, 149.6, 145.5, 134.1, 132.2, 120.1, 119.7, 112.1, 112.0, 107.6, 104.4, 55.7, 55.6, 38.7, 33.7, 31.4, 29.5, 22.8, 9.6; FTIR (KBr) 3303, 2944, 1637, 1553, 1470 cm$^{-1}$.

Anal. Calcd. for C$_{21}$H$_{23}$NO$_3$: C, 73.57; H, 6.94; N, 4.09. Found: C, 73.23; H, 7.00; N, 4.17.

EXAMPLE 6

N-[(2',7'-Dimethoxyspiro[cyclopropane-1,9'-[9H]fluoren]-2-yl)methyl]acetamide A white solid was obtained in 56% after recrystallization from EtOAc; mp=119–120° C.: $^1$H-NMR (CDCl$_3$) δ 7.64 (d, J=8.3 Hz, 1H), 7.59 (d, J=8.3 Hz, 1H), 6.85–6.92 (m, 2H), 6.77 (d, 1H, J=2.3 Hz), 6.49 (d, 1H, J=2.3 Hz), 5.30 (brs, 1H), 4.16–4.26 (m, 1H), 3.84 (s, 3H), 3.81 (s, 3H), 3.17–3.26 (m, 1H), 2.00–2.12 (m, 1H), 1.87–1.92 (m, 1H), 1.79 (s, 3H), 1.64–1.68 (m, 1H); $^{13}$C-NMR (CDCl$_3$) δ 170.0, 159.0, 158.4, 149.6, 145.5, 134.1, 132.2, 120.1, 119.7, 112.1, 112.0, 107.7, 104.5, 55.7, 55.6, 38.6, 33.7, 31.4, 23.2, 22.7; FTIR (KBr) 3264, 2934, 1645, 1558, 1467 cm$^{-1}$;

Anal. Calcd. for C$_{20}$H$_{21}$NO$_3$.0.12 H$_2$O: C, 73.79; H, 6.58; N, 4.30; H$_2$O, 0.66. Found: C, 73.41; H, 6.49; N, 4.23; H$_2$O, 0.40.

EXAMPLE 7

N-[(2',7'-Dimethoxyspiro[cyclopropane-1,9'-[9H]fluoren]-2-yl)methyl]butanamide An off-white solid was obtained in 40% after recrystallization from EtOAc; mp=94–96° C.: $^1$H-NMR (CDCl$_3$) δ 7.66 (d, J=8.3 Hz, 1H), 7.61 (d, J=8.3 Hz, 1H), 6.86–6.94 (m, 2H), 6.80 (d, 1H, J=2.2 Hz), 6.50 (d, 1H, J=2.3 Hz), 5.24 (br s, 1H), 4.17–4.27 (m, 1H), 3.86 (s, 3H), 3.84 (s, 3H), 3.21–3.30 (m, 1H), 2.03–2.15 (m, 1H), 1.88–1.98 (m, 3H), 1.68–1.72 (m, 1H), 1.41–1.58 (m, 2H), 0.77 (t, 3H, J=7.4 Hz); $^{13}$C-NMR (CDCl$_3$) δ 172.9, 159.0, 158.4, 149.6, 145.5, 134.1, 132.3, 120.1, 119.7, 112.1, 112.0, 107.6, 104.4, 55.7, 55.6, 38.7, 38.5, 33.7, 31.4, 22.8, 19.0, 13.5; FTIR (KBr) 3281, 2960, 1637, 1558, 1467 cm$^{-1}$;

Anal. Calcd. for C$_{22}$H$_{25}$NO$_3$.0.08H$_2$O: C, 74.88; H, 7.19; N, 3.97; H$_2$O, 0.41. Found: C, 74.48; H, 7.50; N, 4.06; H$_2$O, <0.10.

EXAMPLE 8

N-[(2',7'-Dimethoxyspiro[cyclopropane-1,9'-[9H]fluoren]-2-yl)methyl]cyclopropane carboxamide An off-white solid was obtained in 48% after recrystallization from EtOAc; mp=143–145° C.: $^1$H-NMR (CDCl$_3$) δ 7.65 (d, J=8.3 Hz, 1H), 7.60 (d, J=8.3 Hz, 1H), 6.86–6.93 (m, 2H), 6.78 (d, 1H, J=2.2 Hz), 6.50 (d, 1H, J=2.2 Hz), 5.48 (br s, 1H), 4.21–4.30 (m, 1H), 3.84 (s, 3H), 3.83 (s, 3H), 3.21–3.31 (m, 1H), 2.04–2.14 (m, 1H), 1.88–1.93 (m, 1H), 1.66–1.70 (m, 1H), 1.06–1.14 (m, 1H), 0.79–0.92 (m, 2H), 0.60–6.67 (m, 2H); $^{13}$C-NMR (CDCl$_3$) δ 173.4, 159.0, 158.4, 149.7, 145.6, 134.1, 132.3, 120.1, 119.7, 112.1, 111.9, 107.8, 104.5, 55.7, 55.6, 38.7, 33.7, 31.6, 22.8, 14.6, 7.3, 7.2; FTIR (KBr) 3314, 2947, 1639, 1557, 1469, 1238, 1040 cm$^{-1}$;

Anal. Calcd. for C$_{22}$H$_{23}$NO$_3$: C, 75.62; H, 6.63; N, 4.01. Found: C, 75.34; H, 6.53; N, 3.93.

EXAMPLE 9

N-[(2',7'-Dimethoxyspiro[cyclopropane-1,9'-[9H]fluoren]-2-yl)methyl]-cyclobutane carboxamide A white solid was obtained in 49% after recrystallization; mp=145–147° C.: $^1$H-NMR (CDCl$_3$) δ 7.64 (d, J=8.3 Hz, 1H), 7.59 (d, J=8.3 Hz, 1H), 6.84–6.91 (m, 2H), 6.78 (d, 1H, J=2.3 Hz), 6.49 (d, 1H, J=2.3 Hz), 5.10 (br s, 1H), 4.13–4.22 (m, 1H), 3.84 (s, 3H), 3.82 (s, 3H), 3.21–3.30 (m, 1H), 2.73 (sextet, J=8.4 Hz, 1H), 1.67–2.15 (m, 9H); $^{13}$C-NMR (CDCl$_3$) δ 174.9, 159.0, 158.4, 149.6, 145.5, 134.0, 132.2, 120.1, 119.7, 112.0 (2), 107.6, 104.4, 55.7, 55.6, 39.7, 38.7, 33.7, 31.4, 25.3, 25.1, 22.9, 18.0; FTIR (KBr) 3310, 2946, 1640, 1552, 1469 cm$^{-1}$;

Anal. Calcd. for $C_{23}H_{25}NO_3$: C, 76.01; H, 6.93; N, 3.85. Found: C, 75.86; H, 6.80; N, 3.75.

EXAMPLE 10

N-[(2',7'-Dimethoxyspiro[cyclopropane-1,9'-[9H]fluoren]-2-yl)methyl]-2,2-dimethylpropanamide A white solid was obtained in 54% after recrystallization from EtOAc; mp=121–122° C.: $^1$H-NMR (CDCl$_3$) δ 7.64 (d, J=8.3 Hz, 1H), 7.59 (d, J=8.3 Hz, 1H), 6.84–6.91 (m, 2H), 6.78 (d, 1H, J=2.3 Hz), 6.50 (d, 1H, J=2.3 Hz), 5.29 (br s, 1H), 4.07–4.17 (m, 1H), 3.83 (s, 3H), 3.82 (s, 3H), 3.22–3.31 (m, 1H), 2.03–2.12 (m, 1H), 1.92–1.96 (m, 1H), 1.73–1.77 (m, 1H), 0.91 (s, 9H); $^{13}$C-NMR (CDCl$_3$) δ 178.3, 159.0, 158.5, 149.6, 145.5, 134.0, 132.1, 120.1, 119.7, 112.2, 112.1, 107.3, 104.4, 55.7, 55.6, 39.2, 38.4, 33.6, 31.3, 27.3, 23.3; FTIR (KBr) 3339, 2957, 1633, 1529, 1468 cm$^{-1}$;

Anal. Calcd. for $C_{23}H_{27}NO_3$: C, 75.59;H, 7.45; N, 3.83. Found: C, 75.27; H, 7.22; N, 3.72.

EXAMPLE 11

2-Fluoro-7-methoxy fluorenone

The desired material was obtained quantitatively as an orange solid (mp=116–118° C.). $^1$H-NMR (CDCl$_3$) δ 7.26 (d, J=8.2 Hz, 1H), 7.20–7.27 (m, 1H), 7.17–7.19 (m, 1H), 7.09 (d, 1H J=2.4 Hz), 7.20 (dt, 1H, J=8.5, 2.4 Hz), 6.89 (dd, 1H, J=8.2, 2.5 Hz), 3.77 (s, 1H); FTIR (KBr) 1716, 1612, 1474 cm$^{-1}$.

EXAMPLE 12 cis-N-[(2'-Fluoro-7'-methoxy-spiro[cyclopropane-1,9'-[9H]fluoren]-2-yl)methyl]propanamide The diastereomer of 2'-fluoro-7'-methoxyspiro[cyclopropane-1,9'-[9H]fluoren]-2-nitrile with the lower Rf value on TLC (30% EtOAc/ Hexanes, silica gel) was purified by silica gel column chromatography using an ethyl acetate/hexanes gradient (35% yield for two steps). mp=121–123° C. $^1$H-NMR CDCl$_3$) δ 7.62–7.66 (m, 2H), 7.04–7.14 (m, 2H), 6.93 (dd, 1H, J=8.4, 2.3 Hz), 6.46 (d, 1H, J=2.3 Hz), 3.83 (s, 3H), 2.38 (dd, J=9.2, 7.2 Hz, 1H), 2.08–2.20 (m, 2H); FTIR (KBr) 2237, 1626, 1582, 1467 cm$^{-1}$;

Anal. Calcd. for $C_{17}H_{12}NOF$: C, 76.97; H, 4.56; N, 5.28. Found: C, 76.77;H, 4.52; N, 5.21.

Reduction of the nitrile as described provided the amine as the hydrochloride salt in 33% yield (mp>250° C.). $^1$H-NMR (DMSO) δ 8.39 (br s, 2H), 7.82–7.87 (m, 1H), 7.79 (d, 1H, J=8.4 Hz), 7.37 (dd, 1H, J=9.9, 2.3 Hz), 7.14–7.20 (m, 1H), 6.92 (dd, 1H, J=8.4, 2.3 Hz), 6.70 (d, 1H, J=2.2 Hz), 3.79 (s, 3H), 3.05–3.30 (m, 2H), 2.14–2.24 (m, 1H), 2.04–2.06 (m, 2H); FTIR (KBr) 3421, 2999, 1615, 1588, 1465 cm$^{-1}$.

Acylation of the amine provided the final product after recrystallization from ethyl acetate. mp=145–146° C. $^1$H-NMR (CDCl$_3$) δ 7.65–7.68 (m, 1H), 7.63 (d, J=8.3 Hz, 1H), 7.01–7.08 (m, 1H), 6.93 (dd, J=9.3, 2.3 Hz, 1H), 6.89 (dd, J=8.4, 2.3 Hz, 1H), 6.50 (d, 1H, J=2.3 Hz), 5.32 (br s, 1H), 4.06–4.21 (m, 1H), 3.83 (s, 3H), 3.17–3.26 (m, 1H), 1.90–2.17 (m, 4H), 1.69–1.74 (m, 1H), 0.99 (t, 3H, J=7.5 Hz); FTIR (KBr) 3250, 3079, 2938, 1640, 1614, 1564, 1466 cm$^{-1}$;

Anal. Calcd. for $C_{20}H_{20}NO_2F.0.10\ H_2O$: C, 73.42; H, 6.22; N, 4.28.

Found: C, 73.37; H, 6.32; N, 4.07.

EXAMPLE 13 trans-N-[(2'-Fluoro-7'-methoxy-spiro[cyclopropane-1,9'-[9H]fluoren]-2-yl)methyl]propanamide The diastereomer of 2'-fluoro-7'-methoxyspiro[cyclopropane-1,9'-[9H]fluoren]-2-nitrile with the higher Rf value on TLC (30% EtOAc/Hexanes, silica gel) was purified by silica gel column chromatography using an ethyl acetate/hexanes gradient (35% yield for two steps). mp=162–163° C. $^1$H-NMR (CDCl$_3$) δ 7.59–7.65 (m, 2H), 7.02–7.09 (m, 1H), 6.99 (dd, 1H, J=8.4, 2.3 Hz), 6.89 (d, 1H, J=2.3 Hz), 6.62 (dd, 1H, J=8.5, 2.3 Hz), 3.87 (s, 3H), 2.37 (dd, J=9.2, 7.2 Hz, 1H), 2.08–2.19 (m, 2H); FTIR (KBr) 2237, 1622, 1582, 1468 cm$^{-1}$;

Anal. Calcd. for $C_{17}H_{12}NOF$: C, 76.97; H, 4.56; N, 5.28. Found: C, 76.82; H, 4.68; N, 5.29.

Reduction of the nitrile as described provided the amine as the hydrochloride salt in 33% yield (mp>250° C.). $^1$H-NMR (DMSO) δ 8.06 (br s, 1H), 7.79–7.85 (m, 2H), 6.95–7.15 (m, 4H), 3.82 (s, 3H), 3.08–3.28 (m, 2H), 2.00–2.21 (m, 3H); FTIR (KBr) 3411, 2993, 1466 cm$^{-1}$;

Anal. Calcd for $C_{17}H_{16}NOF.1.06\ HCl.0.14\ H_2O$: C, 65.78; H, 5.63; N, 4.51.

Found: C, 65.41; H, 5.70; N, 4.45.

The final product was prepared by acylation of the amine as described and isolated by recrystallization from ethyl acetate. mp=138–140° C. $^1$H-NMR (CDCl$_3$) δ 7.61 (d, 1H, J=8.4 Hz), 7.54 (dd, J=8.3, 5.0 Hz, 1H), 6.93 (m, 1H), 6.86 (dd, 1H, J=8.4, 2.3 Hz), 6.74 (d, 1H, J=2.2 Hz), 6.58 (dd, 1H, J=8.9, 2.3 Hz), 5.22 (brs, 1H), 4.02–4.15 (m, 1H), 3.79 (s, 3H), 3.15–3.24 (m, 1H), 1.82–2.07 (m, 4H), 1.63–1.68 (m, 1H), 0.91 (t, 3H, J=7.6 Hz); FTIR (KBr) 3301, 1642, 1550, 1466 cm$^{-1}$.

Reasonable variations, such as those which would occur to a skilled artisan, can be made herein without departing from the scope of the invention.

We claim:

1. A compound of Formula I or a pharmaceutically acceptable hydrate or solvate thereof:

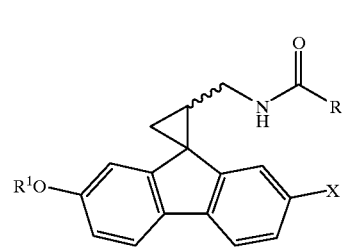

(I)

wherein:

R is $C_{1-4}$ alkyl, $C_{3-6}$ cycloalkyl, $C_{1-3}$ haloalkyl, $C_{1-6}$ alkylamino, di($C_{1-6}$) alkylamino, $C_{3-6}$ cycloalkylamino, $C_{2-6}$ alkenyl, $C_{2-4}$ alkoxyalkyl, $C_{1-4}$ trihalomethylalkyl, or $C_{2-8}$ alkylthioalkyl;

X is C$_{1-4}$ alkoxy, hydrogen or halogen; and

R$^1$ is C$_{1-6}$ alkyl.

2. A compound of claim 1 wherein R is C$_{1-4}$ alkyl and X is C$_{1-4}$ alkoxy.

3. A compound of claim 2 selected from the group consisting of:

N-[(2',7'-dimethoxyspiro[cyclopropane-1,9'-[9H]fluorene]-2-yl)methyl]acetamide;

N-[(2',7'-dimethoxyspiro[cyclopropane-1,9'-[9H]fluoren]-2-yl) methyl]propanamide;

N-[(2',7'-dimethoxyspiro[cyclopropane-1,9'-[9H]fluoren]-2-yl)methyl]butanamide;

(+)-N-[(2',7'-dimethoxyspiro[cyclopropane-1,9'-[9H]fluoren]-2-yl)methyl]propanamide;

(−)-N-[(2',7'-dimethoxyspiro[cyclopropane-1,9'-[9H]fluoren]-2-yl)methyl]propanamide; and N-[(2',7'-dimethoxyspiro[cyclopropane-1,9'-[9H]fluoren]-2-yl)methyl]-2,2-dimethylpropanamide.

4. A compound of claim 1 wherein R is C$_{3-6}$ cycloalkyl and X is C$_{1-4}$ alkoxy.

5. A compound of claim 4 selected from the group consisting of:

N-[(2',7'-dimethoxyspiro[cyclopropane-1,9'-[9H]fluoren]-2-yl)methyl]cyclopropane carboxamide; and N-[(2',7'-dimethoxyspiro[cyclopropane-1,9'-[9H]fluoren]-2-yl)methyl]cyclobutane carboxamide.

6. A compound of claim 1 wherein R is C$_{1-4}$ alkyl and X is halogen.

7. A compound of claim 6 selected from the group consisting of:

cis-N-[(2'-fluoro-7'-methoxy-spiro[cyclopropane-1,9'-[9H]fluoren]-2-yl)methyl]propanamide; and trans-N-[(2'-fluoro-7'-methoxy-spiro[cyclopropane-1,9'-[9H]fluoren]-2-yl)methyl]propanamide.

8. A method of treating sleep disorders in a patient in need of such treatment comprising the step of administering to that patient a therapeutic amount of a compound of claim 1.

9. A pharmaceutical composition comprising a therapeutic amount of a compound of claim 1 and a suitable amount of a pharmaceutically acceptable carrier.

* * * * *